US007149566B2

(12) United States Patent
Lee

(10) Patent No.: US 7,149,566 B2
(45) Date of Patent: Dec. 12, 2006

(54) SOFT TISSUE ORIENTATION AND IMAGING GUIDE SYSTEMS AND METHODS

(75) Inventor: Roberta Lee, Redwood City, CA (US)

(73) Assignee: Manoa Medical, Inc., Redwood City, CA (US)

( * ) Notice: Subject to any disclaimer, the term of this patent is extended or adjusted under 35 U.S.C. 154(b) by 419 days.

(21) Appl. No.: 10/284,990

(22) Filed: Oct. 31, 2002

(65) Prior Publication Data

US 2004/0087851 A1  May 6, 2004

(51) Int. Cl.
*A01B 5/05* (2006.01)
(52) U.S. Cl. ............... 600/429; 600/407; 600/415; 600/417; 600/423; 600/424; 600/427; 128/915; 378/37; 378/62; 378/63
(58) Field of Classification Search ........... 600/407, 600/410, 417, 425, 437, 443, 472, 473, 476
See application file for complete search history.

(56) References Cited

U.S. PATENT DOCUMENTS

| | | | |
|---|---|---|---|
| 4,347,850 A | 9/1982 | Kelly-Fry et al. | |
| 4,478,084 A | 10/1984 | Hassler et al. | |
| 5,146,923 A | 9/1992 | Dhawan | |
| 5,201,742 A | 4/1993 | Hasson | |
| 5,333,612 A | 8/1994 | Wild | |

(Continued)

FOREIGN PATENT DOCUMENTS

DE            3227624         1/1984

(Continued)

Primary Examiner—Brian L. Casler
Assistant Examiner—William Jung
(74) Attorney, Agent, or Firm—Jung-hua Kuo

(57) ABSTRACT

Systems and methods for the orientation of soft tissue such as breast tissue for enhanced accuracy of imaging and/or procedures such as a biopsy or excision are disclosed. The system for orientating and maintaining the orientation of soft tissue generally includes a frame defining an opening, the frame being configured to orient and immobilize an area of soft tissue positioned on one side of the opening, an attachment mechanism to secure the frame to an attachment region defined by the area of soft tissue or by a skin surface overlying the area of soft tissue, to facilitate orienting and immobilizing the area of soft tissue, and an imaging device to image the area of soft tissue. The opening may allow a probe of the imaging device or imaging energy transmitted by the imaging device to be movable therein for image scanning of the soft tissue. The probe, e.g., an ultrasound transducer can be rotated within the frame such that the probe scans at least either of two perpendicular directions within the frame. The frame may be adjustable in at least one dimension in order to adjust the size of the frame opening so as to facilitate the scanning and positioning of the probe within the frame opening. The frame may be attached and secured to the soft tissue with vacuum, adhesive, and/or clips or hooks. The soft tissue may be stretched into a desire orientation prior to attachment of the frame. An anchored lift member may be connected to the frame so as to slightly lift the frame and thus position and immobilize the soft tissue to which the frame is attached. Lifting of the soft tissue improves and enhances a tissue separation process using a tissue separation device. A connector may connect the imaging device to the tissue separation device to maintain a portion of the tissue separation device within the image plane of the probe to further improve and enhance the tissue separation process.

46 Claims, 4 Drawing Sheets

U.S. PATENT DOCUMENTS

| | | |
|---|---|---|
| 5,499,989 A | 3/1996 | LaBash |
| 5,678,549 A | 10/1997 | Heywang-Koebrunner et al. |
| 5,702,405 A | 12/1997 | Heywang-Koebrunner et al. |
| 5,709,206 A | 1/1998 | Teboul |
| 5,855,554 A | 1/1999 | Schneider et al. |
| 5,913,863 A | 6/1999 | Fischer et al. |
| 6,122,542 A | 9/2000 | Lee et al. |
| 6,146,377 A | 11/2000 | Lee et al. |
| 6,254,614 B1 | 7/2001 | Jesseph |
| 6,273,862 B1 | 8/2001 | Privitera et al. |
| 6,277,083 B1 | 8/2001 | Eggers et al. |
| 6,304,770 B1 * | 10/2001 | Lee et al. .................. 600/427 |
| 6,334,847 B1 | 1/2002 | Fenster et al. |
| 6,342,891 B1 | 1/2002 | Fenster et al. |
| 6,355,049 B1 | 3/2002 | Gill |
| 6,361,493 B1 | 3/2002 | Spence et al. |
| 6,406,424 B1 | 6/2002 | Williamson, IV et al. |
| 6,406,482 B1 * | 6/2002 | Chakeres .................. 606/130 |
| 2002/0099264 A1 | 7/2002 | Fontenot |
| 2002/0156376 A1 | 10/2002 | Wang et al. |

FOREIGN PATENT DOCUMENTS

| | | |
|---|---|---|
| EP | 0 331 348 | 9/1989 |
| WO | WO 98/17166 | 4/1998 |

* cited by examiner

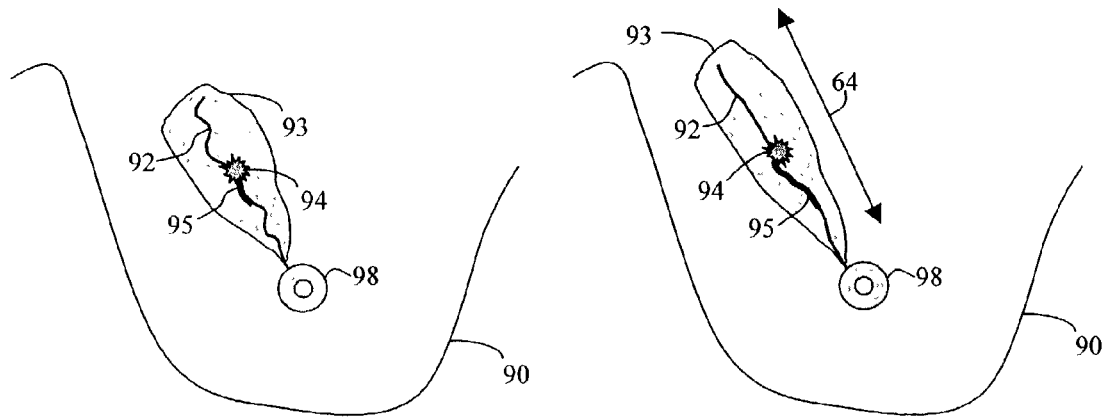
FIG. 4A
FIG. 4B
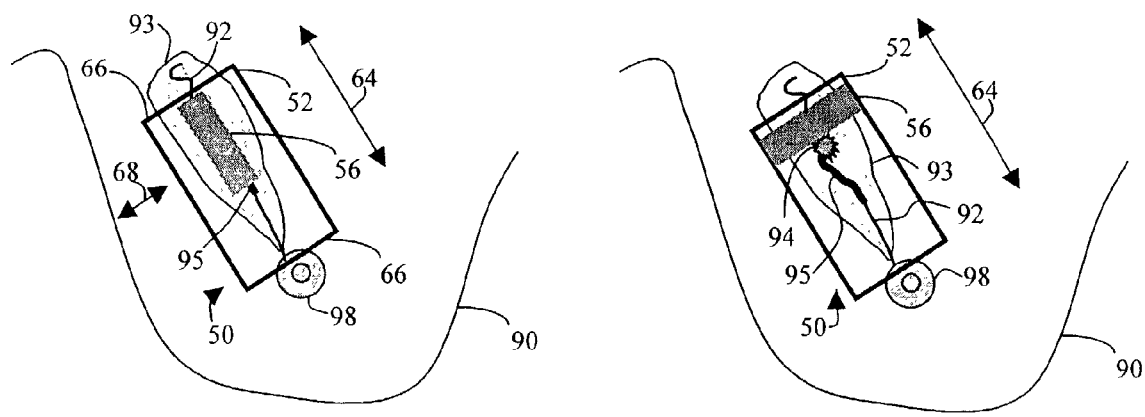
FIG. 4C
FIG. 4D
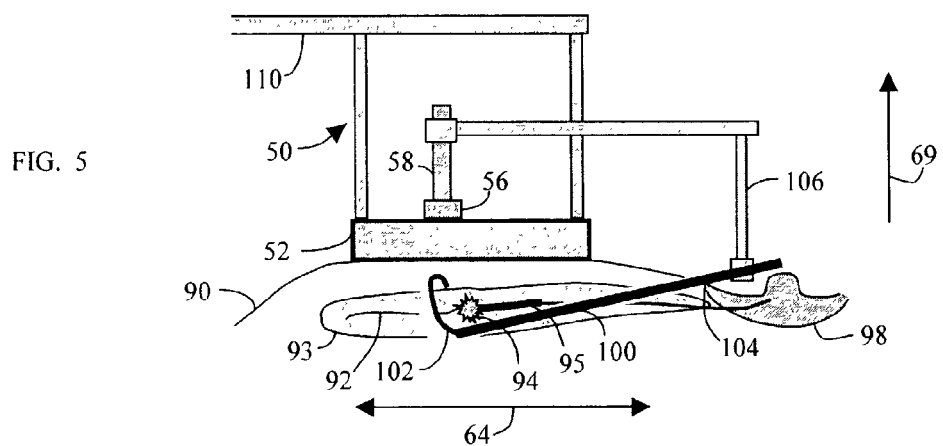
FIG. 5

SOFT TISSUE ORIENTATION AND IMAGING GUIDE SYSTEMS AND METHODS

BACKGROUND OF THE INVENTION

1. Field of the Invention

The present invention relates generally to systems and methods for positioning and maintaining a region of soft tissue in a desired orientation to facilitate imaging, and the performance of a procedure in the soft tissue. More specifically, systems and methods for the orientation of soft tissue such as breast tissue for enhanced accuracy of imaging and/or procedures such as a biopsy or excision are disclosed.

2. Description of Related Art

Before a lesion within breast tissue of a living subject can be properly targeted and treated, the breast tissue is often imaged in order to locate and delineate the lesion. Once the location of the lesion is determined, it is often necessary to insert an invasive device such as a guide wire into the breast tissue to target the lesion. Ideally, the tip of the guide wire is placed near the lesion within the breast tissue. The guide wire helps direct the surgeon to the lesion during an operative procedure.

There are several disadvantages in such a procedure using the guide wire. For example, using a guide wire is a cumbersome and time consuming process. The pre-operative guide wire placement is typically performed in a separate department from the operative procedure, often adding hours of time. In addition, the guide wire can move within the breast before the operative procedure is conducted. Further, only a rough estimate of the actual location of the tip of the guide wire within the breast tissue can be made prior to making the skin incision which often leads to inaccurate or excessive tissue excision.

An imaging process at the time of the operative procedure would eliminate the need for pre-operative guide wire placement and would allow more accurate targeting of the lesion.

From the start of the imaging and localization process to locate the lesion to the completion of the procedure to address the lesion, the breast tissue should be optimally positioned and maintained in the desired orientation during the entire process. For example, if the breast tissue moves after localization of the lesion by imaging and before the procedure, the region of the procedure may not be that of the lesion. Thus, minimally invasive devices and procedures on the breast that require imaging often require breast immobilization.

Conventional breast immobilization devices have resulted from the techniques of mammography in which the breast is compressed and held immobile between two rigid and parallel plates. After using mammography to localize the lesion within the breast, the breast remains compressed and immobilized between the two compression plates to provide a platform from which to conduct the diagnostic procedure. Thus the breast stays in compression during the entire localization and biopsy procedures. However, there are a number of disadvantages with the use of parallel compression plates. For example, such a breast compression device and associated procedures are uncomfortable, awkward, and painful for the patient. In particular, the patient is often required to assume an uncomfortable position to fit the breast between the plates and the degree of compression necessary to properly stabilize the breast in this manner is great. In addition, compression distorts the internal structures of the breast, jeopardizing the accuracy and effectiveness of the procedure. Conventional breast immobilization devices also do not orient the tissue in a manner conducive to providing an optimal site for a skin incision to perform the procedure.

Sonographic localization of the lesion is another method used to target lesions in the breast tissue for sampling or excision. For example, a physician may use ultrasound to guide a fine needle aspiration, core biopsy, or vacuum assisted core biopsy. In such a procedure, rather than compressing the breast, an ultrasound transducer is typically used to image the breast to locate the lesion. In a biopsy guided by ultrasound, the physician needs to simultaneously stabilize the breast, hold the ultrasound transducer, and perform the biopsy accurately enough to obtain tissue from the lesion while maintaining the needle within the imaging plane of the ultrasound transducer. It is difficult for the physician to have an assistant help perform the procedure because the ultrasound transducer and biopsy device need to be in precise alignment in order for the biopsy device to be visualized on the ultrasound monitor. Furthermore, the breast moves in response to even slight pressure or patient movement due to, for example, coughing or even the patient's heartbeat. Such movement may make imaging and targeting of a lesion during a procedure in the breast difficult and may also cause the biopsy device and ultrasound transducer to misalign.

Nonetheless, such sonographic imaging and procedures on an uncompressed breast would generally be more comfortable for the patient, may allow more entry site choices for the surgical device, and may provide for excising of tissue from the breast in its natural state. One example of an ultrasound examination of the breast is described in U.S. Pat. No. 5,709,206 to Teboul, the entirety of which is incorporated by reference herein. In particular, Teboul describes utilizing ultrasound examination of the internal breast anatomy to study the lesion and its relation to the duct in which it developed. By using axial ductal ultrasound scanning, identification and characterization of the lesion, position within the lobe, and the possibility of spread within the duct or ducts and/or the identification other lesions within the affected lobe (e.g. multifocal cancer) can be delineated prior to a biopsy or treatment procedure. In order to facilitate identification and characterization of the ducts, the ducts should ideally be in a straight alignment with the length of the ultrasound transducer such that as much of the length of the duct as possible is within the imaging plane of the transducer. The ducts can be straightened manually by applying slight pressure using a transducer with a length of at least 6 cm. Maintaining the ducts as straight as possible during an invasive procedure would facilitate the accuracy and ease of the procedure.

Accordingly, there is a need for a system and method for orienting the soft tissue in an area of the breast or other soft tissue and for maintaining or immobilizing the soft tissue in the desired orientation that enhance accuracy of imaging and/or procedures. Ideally, the system and method allow imaging of a procedure as it is being performed for improved effectiveness and accuracy of the procedure.

SUMMARY OF THE INVENTION

Systems and methods for the orientation of soft tissue such as breast tissue for enhanced accuracy of imaging and/or procedures such as a biopsy or excision are disclosed. It should be appreciated that the present invention can be implemented in numerous ways, including as a process, an apparatus, a system, a device, or a method. Several inventive embodiments of the present invention are described below.

The system for the orientation of soft tissue generally includes a frame to position and maintain the soft tissue in a desired orientation, an imaging device, and an opening defined by the frame which generally outlines the area of soft tissue to be oriented and imaged. The area of soft tissue is positioned in a desired orientation and immobilized in that orientation with the frame. The frame may be attached and secured to the soft tissue or skin with vacuum, adhesive, and/or clips or hooks. An anchored lift member may be connected to the frame so as to lift the frame and thus the soft tissue to which the frame is attached. Lifting of the soft tissue further immobilizes the soft tissue from extraneous movement and also improves and enhances a tissue separation process using a tissue separation device. The opening may receive a probe of the imaging device or the imaging energy of the imaging device. The opening in the frame is sized to allow the probe to be movable therein for image scanning of the soft tissue. The probe, e.g., an ultrasound transducer, can be rotated within the frame such that the probe scans within the frame preferably in either of two perpendicular directions. The frame may be adjustable in at least one dimension in order to adjust the size of the frame opening so as to facilitate the scanning and positioning of the probe (or the imaging energy of the imaging device) within the frame opening. Alternatively, the imaging beams may pass through the frame or beneath the frame. A connector may connect the imaging device to the tissue separation device to maintain a portion of the tissue separation device within the imaging plane of the imaging device to further improve and enhance the tissue separation process.

A method for orienting and imaging soft tissue generally includes scanning the soft tissue with an imaging device, determining the area of soft tissue of interest, placing a frame of an orientation apparatus to the area of soft tissue or a skin surface overlying the area of soft tissue, and positioning the area of soft tissue in a desired orientation. Furthermore, a lift member may be used to raise the frame which causes the attached area of soft tissue to be stretched away from underlying structures. This provides additional immobilization and may enhance the tissue separation process. In one embodiment, an imaging probe is positioned in an opening defined by the frame where the frame is optionally sized to allow the probe to change orientation therein for image scanning of the area of soft tissue in either of two perpendicular directions. Alternatively, rather than positioning the probe within the opening, the imaging device may be positioned outside of the opening such that the imaging beams or energy transmitted and/or received by the imaging device pass through the opening of the frame, through the frame, itself, or beneath the frame to allow imaging of the area of soft tissue.

The step of determining the area of soft tissue to be oriented preferably includes imaging, i.e., without the frame, of the soft tissue. Before securing the frame to the soft tissue, the frame can be immobilized (e.g. manually) over the area of soft tissue and the area of soft tissue rescanned with the imaging device to ensure correct placement of the frame. The area of soft tissue may be positioned in the desired orientation prior to attaching the frame or in an alternative, the frame may be attached prior to positioning the area of soft tissue in the desired orientation. In the latter, the frame when attached to the area of soft tissue or the overlying skin surface can be adjusted in one or more dimensions to position the area of soft tissue in the desired orientation.

The method for orienting and imaging soft tissue may be adapted to or incorporated into a tissue severing process. The tissue severing process additionally includes inserting a tissue separation device into the soft tissue, positioning the tissue separation device guided by imaging, and moving the tissue separation device guided by imaging to separate the soft tissue.

The apparatus provides an operative framing system that can hold an imaging probe, e.g. an ultrasound transducer, while maintaining the orientation of the area of soft tissue to prevent undesirable movement. Such apparatus improves imaging and the tissue separation procedure by positioning the area of soft tissue in a better geometric arrangement, for example, stretching the tissue along the direction of the duct(s) to straighten the duct(s). Furthermore, the apparatus additionally improves the tissue separation procedure by stretching the soft tissue in another direction or directions, for example, by lifting the breast away from the chest wall, to provide traction and counter traction. Once the soft tissue area of interest is in the desired orientation, the apparatus immobilizes and keeps the area of interest in the desired orientation during imaging and the tissue separation procedure.

These and other features and advantages of the present invention will be presented in more detail in the following detailed description and the accompanying figures which illustrate by way of example the principles of the invention.

BRIEF DESCRIPTION OF THE DRAWINGS

The present invention will be readily understood by the following detailed description in conjunction with the accompanying drawings, wherein like reference numerals designate like structural elements, and in which:

FIG. 4A is a schematic illustrating a lesion in a duct of a breast;

FIG. 4B is a schematic illustrating effect of stretching the duct and the lobe in which the duct is located;

FIG. 4C is a schematic illustrating the positioning of the probe within the frame secured to the breast to maintain the orientation of the breast in order to image the duct, the lobe, and/or the lesion;

FIG. 4D is a schematic illustrating an alternative positioning of the probe within the frame in order to image the duct, the lobe, and/or the lesion;

FIG. 5 is a schematic illustrating the stabilizing holder device used in conjunction with a tissue separation device and a lift member.

DESCRIPTION OF SPECIFIC EMBODIMENTS

Systems and methods for the orientation of soft tissue such as breast tissue for enhanced accuracy of imaging and/or procedures such as a biopsy or excision are disclosed. The following description is presented to enable any person skilled in the art to make and use the invention. Descriptions of specific embodiments and applications are provided only as examples and various modifications will be readily apparent to those skilled in the art. The general principles defined herein may be applied to other embodiments and applications without departing from the spirit and scope of the invention. Thus, the present invention is to be accorded the widest scope encompassing numerous alternatives, modifications, and equivalents consistent with the principles and features disclosed herein. For purpose of clarity, details relating to technical material that is known in the technical fields related to the invention have not been described in detail so as not to unnecessarily obscure the present invention.

Figure 1:
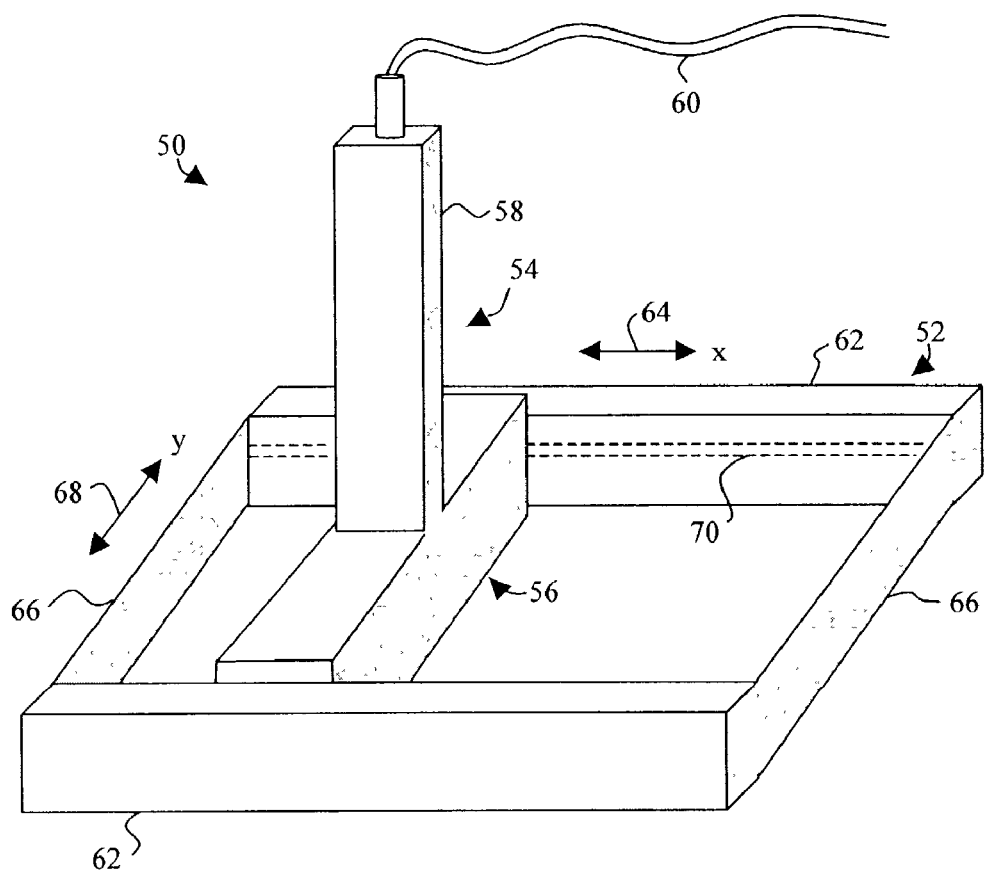
FIG. 1 is a perspective view of an exemplary embodiment of a stabilizing holder device particularly suitable for stabilizing soft tissue such as the breast or an area of the breast.

FIG. 1 is a perspective view of an exemplary embodiment of an orientation device 50 particularly suitable for orienting or positioning and immobilizing soft tissue such as the breast or an area of the breast. Although the preferred use is for imaging and procedures in the breast, as given by example, the tissue site of use is not limited to the breast. The embodiments and methods described herein can be used in and not limited to other tissues such as other subcutaneous tissue, heart, and liver. The orientation device 50 generally comprises a frame 52 defining an opening to allow imaging of the area of soft tissue therethrough using an imaging apparatus 54 such as an ultrasound transducer. Although the examples presented herein utilize ultrasound, it is to be understood that any other suitable imaging methods may be utilized. The imaging apparatus 54 preferably includes a probe 56, a handle 58, and a transmission mechanism 60 for transmitting image data to a computer system (not shown) for data processing and display, for example. The transmission mechanism 60 may be a cable connection, as shown, wireless, or any other suitable mechanism.

In the embodiment shown in FIG. 1, the probe 56 is positioned within the opening of the frame 52. However, it is to be understood that the imaging apparatus 54 may be positioned outside of the frame 52 such that the imaging beams or energy transmitted and/or received by the imaging apparatus 54 pass through the opening of the frame 52 to allow imaging of the area of soft tissue therethrough or that the imaging beams or energy transmitted may pass underneath the opening of the frame 52 or through the frame 52 to allow imaging of the soft tissue beneath the opening of the frame 52. Such a configuration may be employed, for example, when imaging with a MRI (magnetic resonance imaging), CT (computed tomography), PET (positron emission tomography), nuclear medicine, or X-ray imaging device. In a further embodiment, the imaging apparatus 54 may be configured to produce three-dimensional images of the area of soft tissue.

The frame 52 may comprise two generally parallel cross members 62 along its length in the X direction 64 and two connecting strips 66 along its width in the Y direction 68. The connecting strips 66 connect the two parallel cross members 62 to form a generally rectangular frame 52. The cross members 62 and connecting strips 66 may be made of any suitable material or combination of materials such as plastics, metals, or ceramics. Although shown as separate components, the cross members 62 and connecting strips 66 may be integrally formed.

Figure 2:
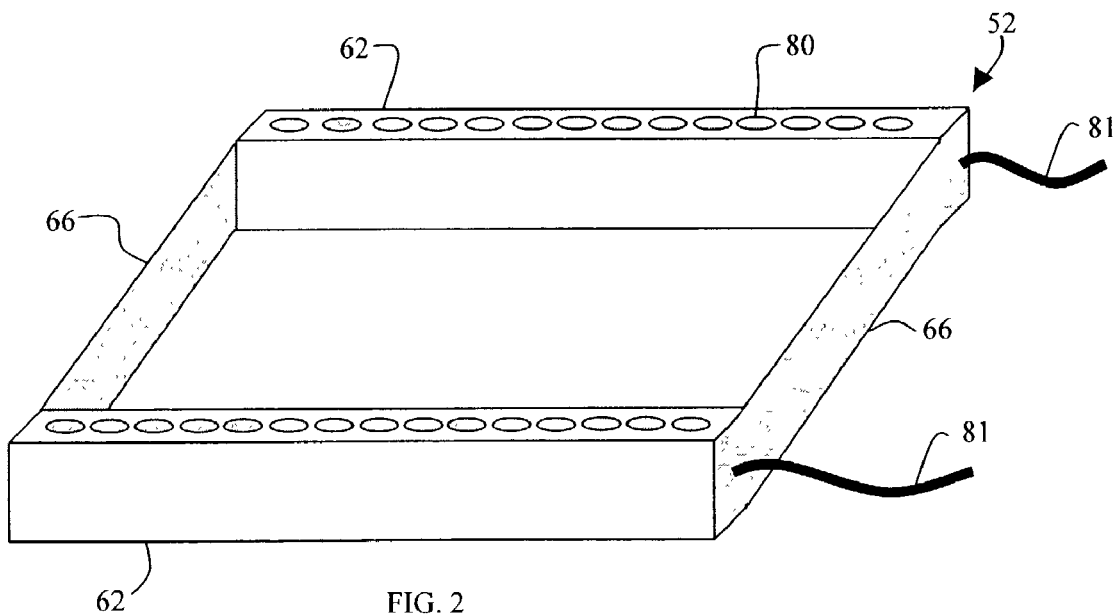
FIG. 2 is a bottom view of a frame of the stabilizing holder device illustrating, as an example, vacuum ports for facilitating attachment of the stabilizing holder device to the breast or other area being examined.
Figure 3A:
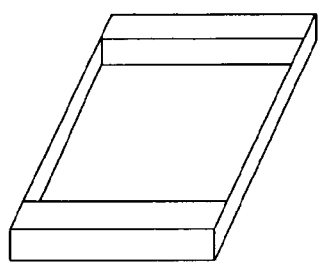
FIGS. 3A–3I are perspective views illustrating various exemplary configurations of the frame of the stabilizing holder device.
Figure 3B:
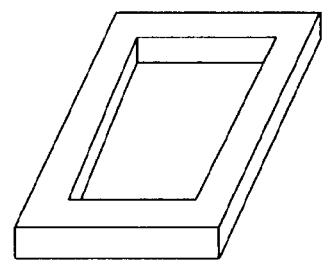
Figure 3C:
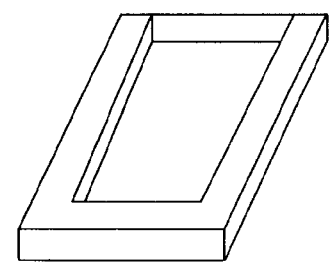
Figure 3D:
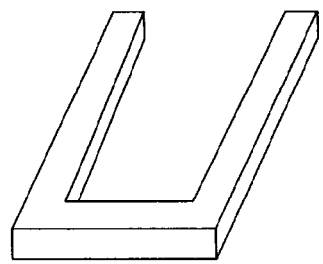
Figure 3E:
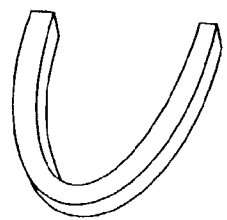
Figure 3F:
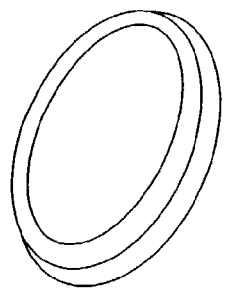
Figure 3G:
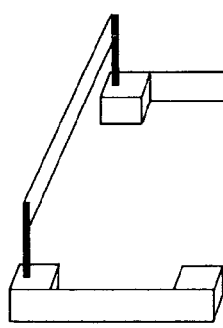
Figure 3H:
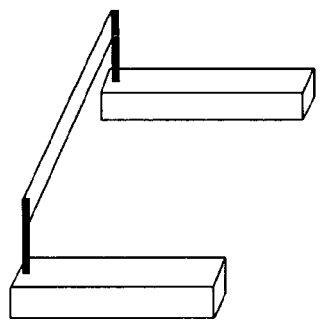
Figure 3I:
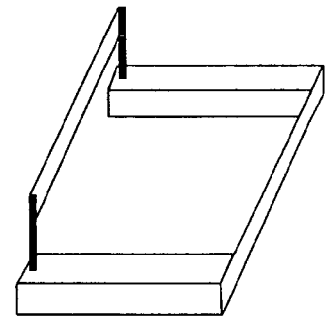

The cross members 62 and/or connecting strips 66 preferably provide a mechanism to attach or adhere the frame 52 to the breast or other area being examined. Once the frame 52 is attached to the desired area, the frame 52 stays fixed in place relative to the skin or soft tissue to which it is attached. Examples of suitable attachment mechanisms include adhesive, vacuum, and/or hooks or clips. FIG. 2 is a bottom view of the frame 52 illustrating, as an example, vacuum ports 80 for facilitating attachment of the orientation device to the breast or other area being examined. As is evident, where vacuum is used, the vacuum ports are preferably provided on surfaces of the cross members 62 that contact the skin or soft tissue of the patient. The frame 52 is connected to an external vacuum source (not shown) using vacuum tubes 81. Similarly, where an adhesive is used, the adhesive is preferably applied on surfaces of the cross members 62 that contact the skin of the patient. The cross members 62 provide greater surface area than the connecting strips 66. Where hooks are utilized, the hooks are preferably provided along at least a portion of the perimeter of the frame 52.

In the embodiment shown in FIG. 1, the cross members 62 provide more dimensional stability for the frame 52 than the connecting strips 66 due to their relative sizes. FIGS. 3A–3I are perspective views illustrating various other exemplary configurations of the frame. For example, the frame may provide cross members on three or four sides of the frame and only one or no connecting strips, respectively. In addition, there may be multiple cross members linked together by connecting strips. As another example, a squared or rounded U-shaped frame or an oval frame may be provided. The connecting strips may be in the same plane or a different plane relative to the cross members. In addition, the bottom surface of the frame that contacts the skin of the patient need not be flat but may be contoured as desired to achieve better contact and/or be more securely attached to the skin or soft tissue.

Referring again to FIG. 1, the imaging apparatus 54 is movable within the frame 52 so that the imaging apparatus 54 can scan the tissue area within the confines of the frame 52. In the configuration shown in FIG. 1, the probe 56 has a length approximately equal to the interior width of the frame 52 such that the imaging apparatus 54 is slidably movable within the frame 52 between the cross members 62 along the X direction 64 between the connecting strips 66 while the probe 56 stays generally perpendicular to the cross members 62.

It is noted that the frame 52 and/or the imaging apparatus 54 may provide any suitable mechanical mechanism to facilitate movement of the imaging apparatus 54 within the frame 52. For example, one or both of the cross members 62 may provide a groove 70 (shown dashed) and one or both ends of the probe 56 may provide a corresponding mating tongue (not shown) that slides within the groove 70. The tongue(s) provided by the probe 56 may be retractable and/or pliable, for example, to facilitate insertion of each tongue into the corresponding groove. As another example, the probe 56 may additionally or alternatively provide clips that secure the probe 56 to the frame 52 on the exterior sides of the cross members 62. As a further example, the frame 52 may provide a holder (not shown) for holding the probe 56 within the frame 52. The holder may be movable within the opening of the frame 52 such that when the probe 56 is held by the holder, the probe 56, along with the holder, is movable relative to and within the frame 52. Similar mechanisms may be provided to facilitate movement of the imaging apparatus 54 relative to the frame 52 where the imaging device is positioned outside of the opening of the frame 52.

As noted above, the probe 56 may be positioned within the opening of the frame 52 and manually moved within the frame. However, the imaging device 54 need not be confined within the frame, but rather, the imaging device 54 may be positioned and mounted outside of the frame 52 such that the imaging beams or energy transmitted and/or received by the imaging device 54 pass through the opening of the frame 52, through the frame 52, or under the frame 52 to allow imaging of the soft tissue beneath the frame 52. Such a configuration may be employed, for example, with MRI, CT, PET, nuclear medicine, or an X-ray imaging device. With the scanning energy rather than the probe being within the opening of the frame 52, one dimension of the opening is preferably sized in one dimension at least equal to the scanning length of the imaging device 54.

The length of the frame 52 may be fixed in size or may be adjustable in one or two directions. As shown in FIG. 1, the interior width of the frame 52 is approximately equal to the length of the probe 56 such that the probe 56 is slidably movable within the frame in the X direction 64. However, the imaging apparatus 54 may be rotated 90° relative to the frame 52 and the frame 52 may be adjusted to have an interior length approximately equal to length of the probe 56 such that the probe 56 is slidably movable within the frame in the Y direction 68.

In one embodiment, the frame 52 may be adjustable in length (X direction 64) by having one or more retractable/extensible portions retractable into and extensible from a fixed portion of the cross members 62. Alternatively or additionally, one or both connecting strips 66 may be slidable along the inside length of the cross members 62 so as to adjust the length of the frame 52. Similarly, the frame 52 may be additionally or alternatively adjustable in width. Width adjustment of the frame 52 may be provided in any suitable manner such as those described above with respect to length adjustment of the probe 56. For example, the connecting strips 66 may provide one or more retractable/extensible portions retractable into and extensible from a fixed portion of the connecting strips 66. Alternatively or additionally, one or both cross members 62 may be slidable along the length of the connecting strips 66 so as to adjust the width of the frame 52. As yet another example, one or both of the cross members 62 may be detachably mounted to the connecting strips 66 such that the detachable cross members 62 can be detached from and remounted to the connecting strips 66 at a different location. Although specific examples of length and width adjustments of the frame 52 are presented herein, adjustment of the length and/or width of the frame 52 may be provided in any suitable manner. For example, rather than adjusting the dimensions of the frame 52, the size of the probe 56 may be adjusted, the probe 56 may be placed inside an adaptor and positioned within the frame 52, or the probe may be replaced with a different sized probe.

One preferred use of the orientation device 50 is for positioning, immobilizing, and ultrasonically imaging an area of the breast and optionally performing a biopsy or other tissue separation and extraction procedure guided by the ultrasound imaging of the internal breast anatomy. The biopsy preferably includes the removal of a lesion or part of the lesion. Another preferred use of the orientation device 50 is the positioning, immobilizing, and ultrasonically imaging an area of the breast to perform excision of a cancerous lesion. This preferably includes the removal of the cancerous lesion as well as any extension of the cancer within the affected duct or ducts to include an entire lobe of the breast or portion of a lobe.

To encompass the entire cancerous lesion and possible extension of cancer within the associated duct or ducts, the interior dimensions of the frame 52 are preferably 5–10 cm in length and 4–8 cm in width. Linear array ultrasound transducers used for breast imaging are typically 4 cm in length although other sizes, typically 4–8 cm, may be employed. Moreover, the imaging plane for the ultrasound transducer is typically approximately 1 mm in width.

FIGS. 4A–4D illustrate a lesion 94 that has developed within a breast 90 and positioning and securing of the orientation device 50 to immobilize and scan the area of the breast 90 containing the lesion 94. In particular, FIG. 4A is a schematic illustrating the lesion 94 in a duct 92 of the breast 90. As shown, the lesion 94 has developed in the duct 92 of a lobe 93 and a lesion extension 95 has grown within the duct 92 towards the nipple/areolar complex 98. Preferably, prior to attaching the frame to the breast 90, the area of soft tissue containing the lobe 93 is stretched (e.g., manually) as shown in FIG. 4B so that the duct 92 and the lobe 93 containing the duct 92 are elongated to straighten the duct 92. In particular, the area of soft tissue is preferably stretched in the direction 64 prior to placement of the frame for better imaging and targeting of the lesion and/or duct, for example.

FIG. 4C is a schematic illustrating the frame 52 secured to the breast 90 to immobilize and maintain the orientation of the area of soft tissue in the stretched state. As shown, the frame 52 is generally positioned over the area of soft tissue containing the duct 92 and the lobe 93. In addition, the portion of the duct 92 not under the frame 52 has been released from being stretched and thus has returned to its natural state as it is no longer stretched or straightened. In contrast, the portion of the duct 92 under the frame 52 is maintained in the stretched and straightened orientation.

The probe 56 is positioned within the frame 52 so as to image the duct 92, the lobe 93, and/or the lesion 94. The lesion 94 is hidden under the probe 56 in FIG. 4C. As shown, the probe 56 is positioned generally parallel to the duct 92 and perpendicular to the connecting strips 66 such that the probe 56 may move in the direction 64 generally parallel to the duct 92 or in the direction 68 generally perpendicular to the duct 92. The probe 56 may also be angled relative to the underlying soft tissue to change the image plane without moving the probe in any one direction.

As is evident, the probe 56 may be positioned in any direction in relation to the lesion 94, duct 92, or lobe 93. Typically, the probe 56 is positioned in one of two ways within the frame 52 depending on, for example, the desired scan path of the probe 56. For example, the probe 56 is positioned in the configuration shown in FIG. 4C during insertion and positioning of a tissue separation device near the lesion 94 while the probe 56 is positioned in the configuration shown in FIG. 4D once the tissue separation device is properly positioned.

FIG. 4D is a schematic illustrating the probe 56 positioned generally parallel to the connecting strips 66 and perpendicular to the duct 92 such that the probe 56 may move in the direction 64 generally along the length of the duct 92. For example, the probe 56 may be moved in unison with the tissue separation device performing a biopsy guided by the ultrasound imaging of the internal breast anatomy. The probe 56 is preferably moved in unison with the tissue separation device in order to maintain at least a portion of the tissue separation device within the imaging plane of the probe 56 as the tissue separation device is moved, i.e., during the tissue separation procedure.

FIG. 5 is a schematic illustrating the stabilizing holder device 50 used in conjunction with an exemplary tissue separation device 100 and a lift member 110. As shown, the tissue separation device 100 is inserted through an incision 104 in the breast near the orientation device 50 and the lesion 94 and preferably at the border of the nipple/areolar complex 98. A separation or working end 102 of the tissue separation device 100 may be positioned within the breast in preparation for separating the lesion 94 from the surrounding tissue, guided using ultrasound scanning with the probe 56. The working end 102 of the tissue separation device 100 may be a cutting loop, for example, and may be energized with radio frequency (RF) or other sources of energy or may be a sharp edge.

The probe 56 may help guide the tissue separation device 100 during separation of the lesion by moving in unison with the working end 102 such that the working end 102 is continuously within the imaging plane of the probe 56 during the tissue separation process. To facilitate maintaining the working end 102 within the imaging plane of the probe 56, a connector 106 may connect the probe 56 to the tissue separation device 100. The connector 106 may assume any suitable configuration and may be attached to the probe 56 via the handle 58, for example.

As noted above, for better imaging and targeting of the lesion and/or other tissue, the area of soft tissue is preferably stretched in the direction 64 prior to securing the frame 52. The positioning in the direction 64 straightens the duct 92 in the area of soft tissue to facilitate imaging and tissue separation. In an alternative, the area of soft tissue may be positioned in the desired orientation after the frame 52 is secured by adjusting the frame in one or more dimensions. For example, after the frame 52 is secured, the area of soft tissue may be positioned in the desired orientation by widening and/or lengthening the frame 52 to thereby stretch the area of soft tissue in one or more directions. The breast is also preferably lifted away from the chest wall in direction 69, e.g., approximately 1 to 10 cm. Such positioning by lifting increases the distance between the lesion 94 and/or duct 92 and the overlying skin and underlying chest wall which provides traction and counter traction to enhance and improve the tissue separation procedure.

The lifting may be achieved with the use of a lift member 110 attached on one end to the frame 52 of the orientation device 50 and attached on the other end to a stationary anchoring structure (not shown). The lift member 110 lifts the orientation device 50, e.g. 1 to 10 cm, in order to stretch the area of soft tissue in a direction away from the underlying structures. For example, lifting the lift member 110 may stretch the area of the breast away from the chest wall. The stationary object to which one end of the lift member 110 is attached may be a bed or a table, for example, and provides anchoring support and leverage for the lift member 110.

Figure 6:
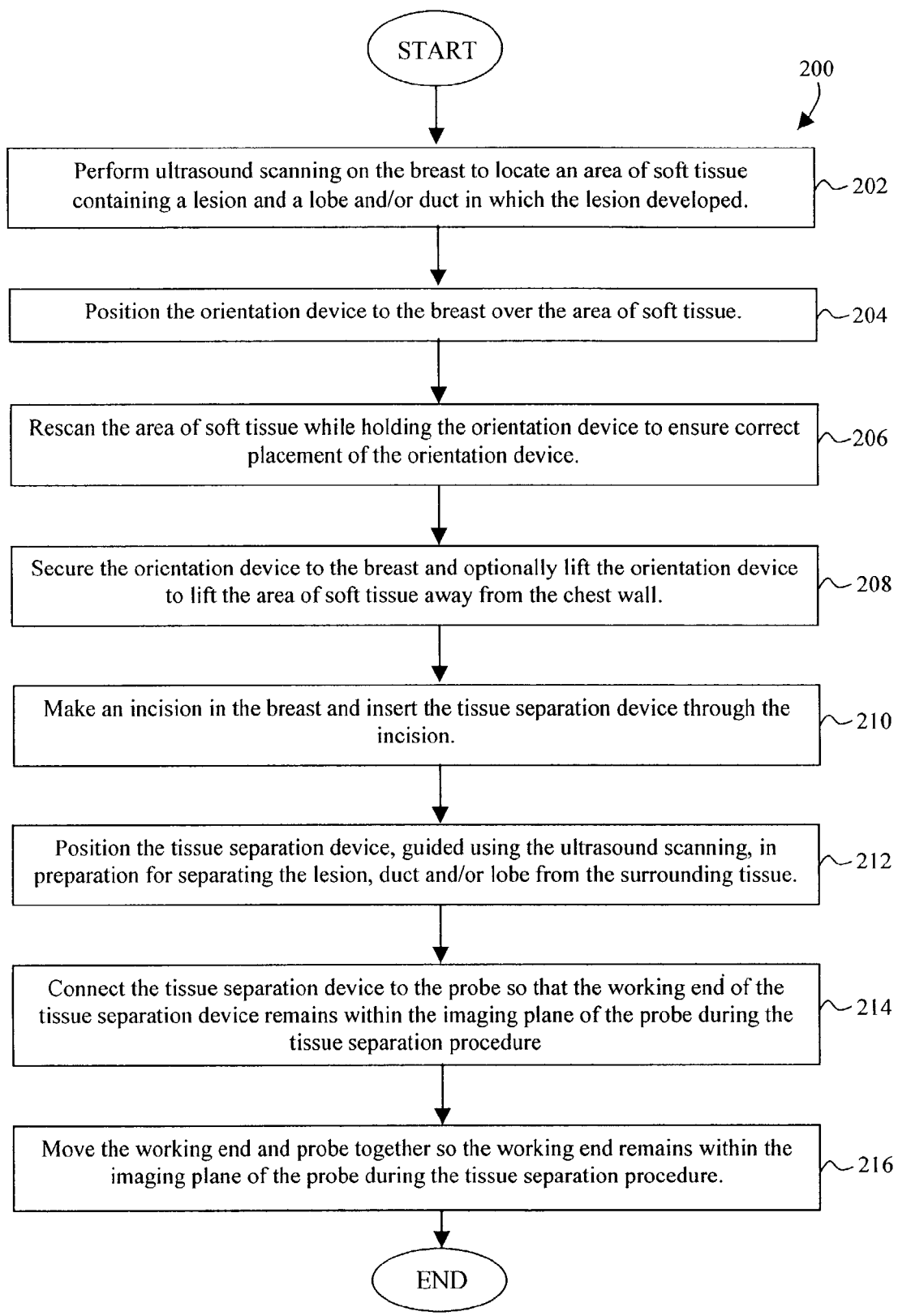
FIG. 6 is a flowchart illustrating an imaging and tissue separation process employing the stabilizing holder device.

FIG. 6 is a flowchart illustrating an example of an imaging and tissue 10 separation process 200 employing the orientation device. At step 202, ultrasound scanning, preferably axial ductal scanning, is performed on the breast to locate a targeted tissue, i.e. a lesion and the duct(s) and/or lobe in which the lesion developed. Preferably, this step is performed free hand, without using the orientation device 50. The axial ductal ultrasound scanning is preferably performed prior to the procedure to identify and delineate the lesion, the affected duct(s) and/or the lobe, the position of the lesion within the duct and/or lobe, and the possibility of other lesions within the affected lobe (e.g. multifocal cancer) and/or spread within the duct(s). The ultrasound imaging method may be enhanced with the use of ultrasound contrast agent, such as described in co-pending U.S. patent application Ser. No. 10,167,017, entitled "Ultrasound Imaging Of Breast Tissue Using Ultrasound Contrast Agent" and filed on Jun. 11, 2002, the entirety of which is incorporated by reference herein.

Once the lesion, duct(s), and/or lobe in which the lesion developed are located, the orientation device is positioned on the breast of the patient over the area of soft tissue containing the lesion, duct(s), and/or lobe at step 204. The area of the breast over which the orientation device is positioned is preferably manually stretched in the desired direction to straighten the duct(s) and/or lobe just prior to positioning the orientation device thereon. The orientation device and the ultrasound transducer may be positioned relative to the duct or lobe similar to that shown in FIG. 4C. In other words, the length of the frame of the device is generally positioned over the length of the duct or lobe while the length of the probe is positioned generally parallel to the length of the duct or lobe such that the probe may move in a direction generally parallel to the duct or lobe. Either the same or a different ultrasound transducer may be used in the orientation device as that used in step 202.

At step 206, the orientation device may be manually held in place while a rescanning of the area of soft tissue is performed to ensure correct placement of the orientation device. At step 208, the orientation device is then secured to the breast with vacuum, adhesives, and/or hooks or clips and may be raised using a lift member so as to stretch the area of soft tissue in a direction away from the chest wall.

At step 210, a tissue separation device is inserted through an incision in the breast. Preferably the incision is made in relatively close proximity to the lesion, duct(s), and/or lobe in which the tissue separation procedure is to be performed and outside of the area held by the orientation device, for example, at the border of the nipple/areolar complex. The tissue separation device may be, for example, a biopsy needle or a tissue severing device such as those described in co-pending U.S. patent application Ser. No. 10,097,412, entitled "Devices And Methods For Tissue Severing And Removal" and filed on Mar. 12, 2002, the entirety of which is incorporated by reference herein.

At step 212, the tissue separation device, guided using ultrasound scanning, is positioned in preparation for separating the lesion, duct(s), and/or lobe from the surrounding tissue. Preferably, the entire lesion, part or all of the associated duct or ducts, or the entire lobe or a part of the lobe containing the lesion is targeted. Once the tissue separation device is properly positioned within the breast tissue, the probe is rotated within the frame of the orientation device relative to the targeted tissue and to the frame similar to that shown in FIG. 4D. In other words, the frame of the orientation device remains in the same orientation relative to the targeted tissue while maintaining the position and immobilization of the desired area of the breast, i.e. the length of the frame is generally oriented over the length of the duct(s) or lobe. In addition, the length of the probe is oriented generally perpendicular to the length of the duct(s) or lobe such that the probe may move in a direction generally parallel to the duct(s) or lobe. Such orientation of the probe allows the width of the lesion, duct(s), lobe or other area of interest to be within the imaging plane.

As is evident, once the orientation device is positioned and secured to the breast over the area of soft tissue located in step 202, the orientation device is fixed to facilitate in positioning, immobilizing, and imaging of the area of soft tissue and guiding the tissue separation procedure. Thus, securing of the orientation device to the breast prevents movement of the area of soft tissue relative to the probe, thereby ensuring a more accurate and effective scanning, lesion targeting, and tissue separation procedure.

At step 214, the tissue separation device may be connected to the probe such that once the tissue separation device is aligned in the imaging plane of the probe, the working end of the tissue separation device will remain within the imaging plane during the tissue separation procedure. In other words, connecting the tissue separation device to the probe helps guide the tissue separation device by maintaining the tissue separation device in the same orientation as the probe.

At step 216, the working end and the probe are moved together so that the working end remains within the imaging plane of the probe during the tissue separation procedure. Where the working end is a cutting ring, the ring may be raised to encircle the lesion, duct(s), lobe, or other targeted tissue and pulled or pushed to cut around the targeted tissue for tissue separation. When the cutter completes the cut around the targeted tissue, the process 200 is complete. In a further embodiment, the severed tissue may be captured in a tissue collection device to facilitate removal from the patient.

As is evident, the orientation device and the imaging and tissue separation process guided using the orientation device provide enhanced accuracy and thus effectiveness in the imaging and the procedure.

While the preferred embodiments of the present invention are described and illustrated herein, it will be appreciated that they are merely illustrative and that modifications can be made to these embodiments without departing from the spirit and scope of the invention. Thus, the invention is intended to be defined only in terms of the following claims.

What is claimed is:

1. An apparatus for orienting and maintaining the orientation of soft tissue, comprising:
   a frame defining an opening, the frame configured lo orient and immobilize an area of soft tissue positioned on one side of the opening, wherein the frame has a first portion and a retractable and extensible portion that is retractable into and extensible from the first portion to provide adjustability in size of the frame;
   an attachment mechanism to secure the frame to an attachment region of soft tissue defined by the area of soft tissue or by a skin surface overlying the area of soft tissue, to facilitate orienting and immobilizing the area of soft tissue; and
   an imaging device to image the area of soft tissue.

2. The apparatus of claim 1, wherein the imaging device transmits a transmission imaging energy for image scanning of the area of soft tissue, the frame and opening being configured such that the transmission imaging energy passes through the opening to facilitate the image scanning of the area of soft tissue.

3. The apparatus of claim 1, wherein the imaging device transmits a transmission imaging energy for image scanning of the area of soft tissue, the frame and opening being configured such that the transmission imaging energy passes beneath or through said frame to facilitate the image scanning of the area of soft tissue.

4. The apparatus of claim 1, wherein the imaging device transmits a transmission imaging energy for image scanning of the area of soft tissue, the imaging device being configured such that the transmission imaging energy is movable relative to said frame.

5. The apparatus of claim 1, wherein the imaging device is in communication with a system for processing image data received from the imaging device and for displaying the processed image data.

6. The apparatus of claim 5, wherein the processed image data is adapted to show a three-dimensional image of the area of soft tissue.

7. The apparatus of claim 1, wherein the imaging device is one of ultrasound, magnetic resonance imaging, computed tomography, positron emission tomography, x-ray imaging, and nuclear medicine imaging.

8. The apparatus of claim 1, wherein the imaging device includes a probe configured to be movable in said opening.

9. The apparatus of claim 8, wherein the probe of the imaging device is an ultrasound transducer.

10. The apparatus of claim 9, wherein the probe has a scanning length and the opening has a first dimension in a first direction at least equal to the scanning length of the probe to facilitate guiding movement of the scanning within the opening in the first direction or in a second direction perpendicular to the first direction.

11. The apparatus of claim 10, wherein the opening has a second dimension in the second direction, the frame being adjustable in the second direction so that the opening has a size in the second direction at least equal to the scanning length of the probe to facilitate guiding movement of the scanning within the opening in the first direction or in the second direction.

12. The apparatus of claim 1, wherein the frame is adjustable in size in a first direction.

13. The apparatus of claim 1, wherein the frame includes a guide member on a surface thereof to guide the probe in its movement along the guide member.

14. The apparatus of claim 13, wherein the guide member is one of a tongue and a groove and wherein the probe provides a corresponding one of a groove and a tongue, respectively, for mating with the guide member of the frame to facilitate guiding movement of the probe along the frame.

15. The apparatus of claim 13, wherein the guide member is a holder for the probe, said holder fitting within the opening of the frame and movable within the opening to facilitate guiding movement of the probe relative to the frame.

16. The apparatus of claim 1, wherein the attachment mechanism comprises vacuum ports on the frame connectable to a vacuum source, said vacuum ports facilitate in attaching the frame to the attachment area.

17. The apparatus of claim 1, wherein the attachment mechanism is an application of adhesive to a surface of the frame to facilitate in attaching the frame to the attachment area.

18. The apparatus of claim 1, wherein the attachment mechanism comprises clips adapted to be clipped to the attachment area to facilitate in attaching the frame to the attachment area.

19. The apparatus of claim 1, further comprising a lift member connected to the frame, the lift member being anchored and adapted to lift the frame and at least one of the skin surface and area of soft tissue to which the frame is attached.

20. The apparatus of claim 19, wherein the lift member is adapted to lift the frame and at least one of the skin surface and the area of soft tissue approximately 1 to 10 cm.

21. The apparatus of claim 1, further comprising a connector for connecting the imaging device to a tissue separation device, the connector facilitates in maintaining at least a portion of the tissue separation device in an imaging plane of the imaging device.

22. The apparatus of claim 21, wherein the imaging device includes a probe configured to be movable in said opening, and wherein the imaging device further includes a handle to facilitate positioning of the probe relative to the frame, wherein the connector is connected to the handle of the imaging device.

23. The apparatus of claim 21, wherein the portion of the tissue separation device imaged by the imaging device is a tissue separator portion of the tissue separation device.

24. A method for orienting and immobilizing a soft tissue, comprising the steps of:
scanning the soft tissue with an imaging device;
determining an area of the soft tissue to be oriented and immobilized;
placing a frame of an orienting and immobilizing apparatus over the area of soft tissue, the frame being configured to be secured to an attachment area of soft tissue defined by the area of soft tissue or by a skin surface overlying the area of soft tissue, wherein the frame has a first portion and a retractable and extensible portion that is retractable into and extensible from the first portion to thereby provide adjustability in size; and
orienting the area of soft tissue by positioning said frame to a desired orientation.

25. The method of claim 24, wherein the imaging device is configured to produce three-dimensional imaging of the area of soft tissue.

26. The method of claim 24, wherein further comprising the step of securing the frame to the attachment area of soft tissue defined by the area of soft tissue or by a skin surface overlying the area of soft tissue by applying at least one of an adhesive, vacuum, and clips between the frame and the attachment area.

27. The method of claim 26, wherein the frame is secured to the attachment area with vacuum using vacuum ports provided by the frame.

28. The method of claim 26, further comprising the step of positioning the area of soft tissue in the desired orientation prior to and during securing the frame to the attachment area.

29. The method of claim 26, further comprising the step of, after the step of securing the frame to the attachment area, positioning the area of soft tissue in the desired orientation by adjusting the size of at least one dimension of the frame.

30. The method of claim 26, further comprising the step of lifting the frame secured to the attachment area with a lift member connected to the frame.

31. The method of claim 30, wherein the step of lifting lifts the frame approximately 1 to 10 cm.

32. The method of claim 24, wherein the imaging device comprises a probe.

33. The method of claim 32, wherein the imaging device is an ultrasound.

34. The method of claim 32, wherein the probe has a scanning length and the opening has a first dimension in a first direction at least equal to the scanning length of the probe to facilitate guiding movement of the scanning by the probe in the first direction or in a second direction perpendicular to the first direction.

35. The method of claim 34, wherein the opening has a second dimension in the second direction, the frame being adjustable in the second direction such that the opening has a size in the second dimension at least equal to the scanning length to facilitate guiding movement of the scanning by the probe in the first or second direction.

36. The method of claim 34, wherein the frame is adjustable in the first direction.

37. A method for imaging, positioning, immobilizing, and performing a tissue severing procedure in soft tissues comprising the steps of:
scanning the tissue with an imaging device;
determining an area of soft tissue to be positioned and immobilized;
placing a frame of an orienting and immobilizing apparatus over the area of soft tissue, the frame being configured to be secured to an attachment area of soft tissue defined by the area of soft tissue or by a skin surface overlying the area of soft tissue, wherein the frame has a first portion and a retractable and extensible portion that is retractable into and extensible from the first portion to thereby provide adjustability in size;
orienting the area of soft tissue by positioning said frame to a desired orientation;
inserting a tissue separation device into the area of soft tissue;
positioning the tissue separation device guided using said scanning; and
moving the tissue separation device guided using said scanning to separate at a least a portion of the area of soft tissue.

38. The method of claim 37, further comprising the step of securing the frame to the attachment area of soft tissue defined by the area of soft tissue or by a skin surface overlying the area of soft tissue.

39. The method of claim 38, wherein the frame is secured to the attachment area after the step of positioning the area of soft tissue to the desired orientation.

40. The method of claim 38, wherein the area of soft tissue is positioned to the desired orientation after the frame is secured to the attachment area by adjusting the size of the frame in at least one dimension.

41. The method of claim 37, further comprising the step of connecting the tissue separation device to the imaging device via a connector to facilitate said moving the tissue separation device and said scanning to maintain at least a portion of the tissue separation device within an imaging plane of the imaging device.

42. The method of claim 41, wherein the portion of the tissue separation device imaged by the imaging device is a tissue separator portion of the tissue separation device.

43. The method of claim 41, wherein the imaging device includes a probe containing a handle to facilitate positioning of said probe within the frame and wherein the connector is connected to the imaging device via the handle.

44. The method of claim 43, wherein the imaging device is an ultrasound.

45. The method of claim 37, wherein the imaging device is configured to produce three-dimensional imaging of the area of soft tissue.

46. The method of claim 37, further comprising the step of raising the frame and the attachment area using a lift member connected to the frame, the lift member being anchored to a stationary anchoring structure.

* * * * *